(12) United States Patent
Hasling (10) Patent No.: US 8,451,448 B1
(45) Date of Patent: May 28, 2013

(54) METHOD AND APPARATUS FOR GENERATING AND POSITIONING MICRO-SCALE EVANESCENT FIELDS

(75) Inventor: Thomas Hasling, Honolulu, HI (US)

(73) Assignee: Oceanit Laboratories, Inc., Honolulu, HI (US)

( * ) Notice: Subject to any disclaimer, the term of this patent is extended or adjusted under 35 U.S.C. 154(b) by 841 days.

(21) Appl. No.: 12/589,017

(22) Filed: Oct. 16, 2009

Related U.S. Application Data (60) Provisional application No. 61/196,300, filed on Oct. 16, 2008.

(51) Int. Cl.
*G01N 21/55* (2006.01)

(52) U.S. Cl.
CPC .................................. *G01N 21/55* (2013.01)
USPC ....................................................... 356/445

(58) Field of Classification Search
CPC ....................................................... G01N 21/55
USPC ................................................. 356/445–448
See application file for complete search history.

(56) References Cited

U.S. PATENT DOCUMENTS

| | | | |
|---|---|---|---|
| 6,645,777 B1 * | 11/2003 | Letcher et al. | 436/526 |
| 7,521,255 B2 * | 4/2009 | Picollet-D'Hahan et al. | 436/172 |
| 7,539,363 B2 * | 5/2009 | Bock et al. | 385/12 |
| 8,247,216 B2 * | 8/2012 | Zaccarin et al. | 435/283.1 |

OTHER PUBLICATIONS

Neher et al.; *The Extracellular Patch Clamp: A Method for Resolving Currents through Individual Open Channels in Biological Membranes*; Pflugers Archive (European Journal of Physiology); 375 (1978); pp. 219-278.

* cited by examiner

*Primary Examiner* — Michael P Stafira
(74) *Attorney, Agent, or Firm* — James Creighton Wray (57) ABSTRACT

Illumination sources are connected to ends of micropipette probes having total internal reflection tips. The total internal reflection produces evanescence at the tips. The evanescence causes fluorescence of dye marked target molecules at tips of the probes. The evanescence is limited to about 100 nm from the tips. The presence of a target molecule at the end of a probe is observed by observing the fluorescence. The limited penetration of the evanescence eliminates noise in the signal and unwanted bleaching of dyes in the cell, so that repeated, multiple and arrays of probes may be applied.

18 Claims, 7 Drawing Sheets

METHOD AND APPARATUS FOR GENERATING AND POSITIONING MICRO-SCALE EVANESCENT FIELDS

This application claims the benefit of U.S. Provisional Application No. 61/196,300, filed Oct. 16, 2008, which is hereby incorporated by reference in its entirety.

TECHNICAL FIELD OF THE INVENTION

The present invention relates to the field of biological imaging and physiology.

BACKGROUND OF THE INVENTION

Several electrophysiology techniques have been used for many years to produce high quality data. Most cellular electrophysiology techniques are either patch clamp or sharp electrode. Patch clamp traditionally uses a glass micropipette, with an open tip diameter of about 1-2 µm. The tip is formed into a smooth surfaced circle. The patch clamp electrode tip is pressed against the cell membrane and suction is applied causing the cell to form a tight seal or "gigaohm seal" with the electrode. This is contrasted by the sharp electrode methods where the electrode is used to impale the cells to conduct traditional intracellular recordings.

The interior of the pipettes are filled with different solutions depending on the specific ion measurements or techniques used. For example, with whole cell recordings, a solution that approximates the intracellular fluids is used. A metal electrode in contact with this solution conducts the electrical signals to an amplifier. The researcher can change the composition of this solution or add drugs to study the ion channels under different conditions. The patch clamp technique was developed in the late 1970s and early 1980s.

Electrophysiology techniques are technically demanding and typically require highly trained operators. The resulting data is of extremely high fidelity; however, this also means that external electrical noises need to be diligently managed. Lighting, electronics, grounding, connections, building wiring, and radio waves can all introduce noise into the system. The electrophysiology electronics and equipment are considerably expensive and technically demanding to assemble and maintain. The micropipettes used for patch clamp are also a point of consideration for the researcher. Typically the researcher fabricates the micropipette and forges the tip at or about the time it is to be used. Additionally, the pipettes need to be carefully filled with the pipette solution. All in all, existing electrophysiology techniques are highly complex and often prohibitively expensive.

A need exists for an improved cellular physiology technique that has lower barriers to entry and is less technically demanding than electrophysiology.

Over the last several years physiologically active dyes have been developed and successfully commercialized to partially address the technical and practical limitations of existing electrophysiology techniques. These dyes are designed to be sensitive to the concentration of specific ion species (e.g. Ca++, Na+, K+). Some of these dyes are sensitive to electrical potential changes.

Most physiologically active dyes are imaged by a technique called ratiometric imaging. Ratiometric imaging relies on the variable excitation properties of the dyes. The dyes preferentially excite at different wavelengths, depending on the concentration of the specific ion or potential. The emission spectrum of the dyes, however, remains the same. By alternating between the excitation wavelengths and correlating the relative emission outputs, the ionic concentrations or electrical potential can be determined and the changes can be plotted over time.

Modern ratiometric illumination systems are capable of alternating at up to 250 cycles/second. Techniques have also been developed that use baseline excitation/emission ratios to calculate the physiologic changes. By comparing the baseline with continuous single wavelength excitation imaging, very high sampling rates can be realized.

The majority of ratiometric imaging systems are constructed around a specialized light source that alternates the excitation energy, a fluorescent microscope, and an intensified CCD video camera system. Alternatively, a confocal microscope system can be configured to do ratiometric imaging. These systems are designed to illuminate the entire cell and capture the resulting images. This becomes problematic over extended imaging periods since the fluorescent dyes are progressively photobleached and the emission strength decreases. Maintaining consistent emission ratios is critical for conducting these techniques. Likewise, once the dyes have been sufficiently bleached, no further data can be gathered.

Needs exist for an improved physiological active dye imaging technique that does not expose the sample with widefield, whole sample, or propagating excitation energy.

Total internal reflection fluorescence microscopy (TIRF) is an technique that allows the researcher to excite a very thin layer of the sample that is in close (~100 nm) proximity to the coverslip or microscope slide. TIRF is accomplished by introduce light into the slide or coverslip at an incident angle that causes the light to be reflected internally. This internal reflection generates an evanescent field on the surface to the glass. The evanescent field will excite appropriate fluorescent molecules if they are within field. As the distance from the glass surface increases, the evanescent field intensity falls exponentially. The practical application of TIRF microscopy provides for a single plane of imaging that is not obscured by objects above and below the focal plane.

Needs exist for user directed, point specific TIRF techniques.

SUMMARY OF THE INVENTION

The present invention is a laser (or other light source) coupled probe that generates a TIRF-based evanescent field on the fine tip. This probe can then be used to selectively excite specific regions of the cell, a whole cell by contacting the cytoplasmic membrane, or other samples. The probe does not penetrate the cell or scan through the cytoplasm. The user will gain the imaging benefits of TIRF without the overhead of a TIRF system. Additionally, the TIRF probe can be used on samples where traditional TIRF would have been difficult or impossible, such as a cell tray.

Traditional TIRF requires specialized optics, geometries, and special materials, which make TIRF highly impractical under less than ideal conditions. This is particularly true for cell trays. The present invention would allow a user of the cell trays to specifically and directly apply a TIRF field to any given well or subsection of a well. When used in conjunction with a computerized positioning system, the optical TIRF probe of the present invention can be used in high throughput application. Additionally, the present invention may be used in conjunction with electrophysiology or on subsections of a cell (e.g. an axon) to observe temporal changes.

The present invention allows the user to conduct point specific TIRF imaging which prevents undesirable photobleaching across the entire sample or field. Another potential application is to use the probe of the present invention to penetrate soft tissue samples and conduct TIRF imaging within the interior of tissue sample (e.g. a brain slice). A user positionable, optical probe can be used to conduct live cell physiological measurements, similar to the way micropipettes are employed for electrophysiology.

Figures 1A, 1B, 2:
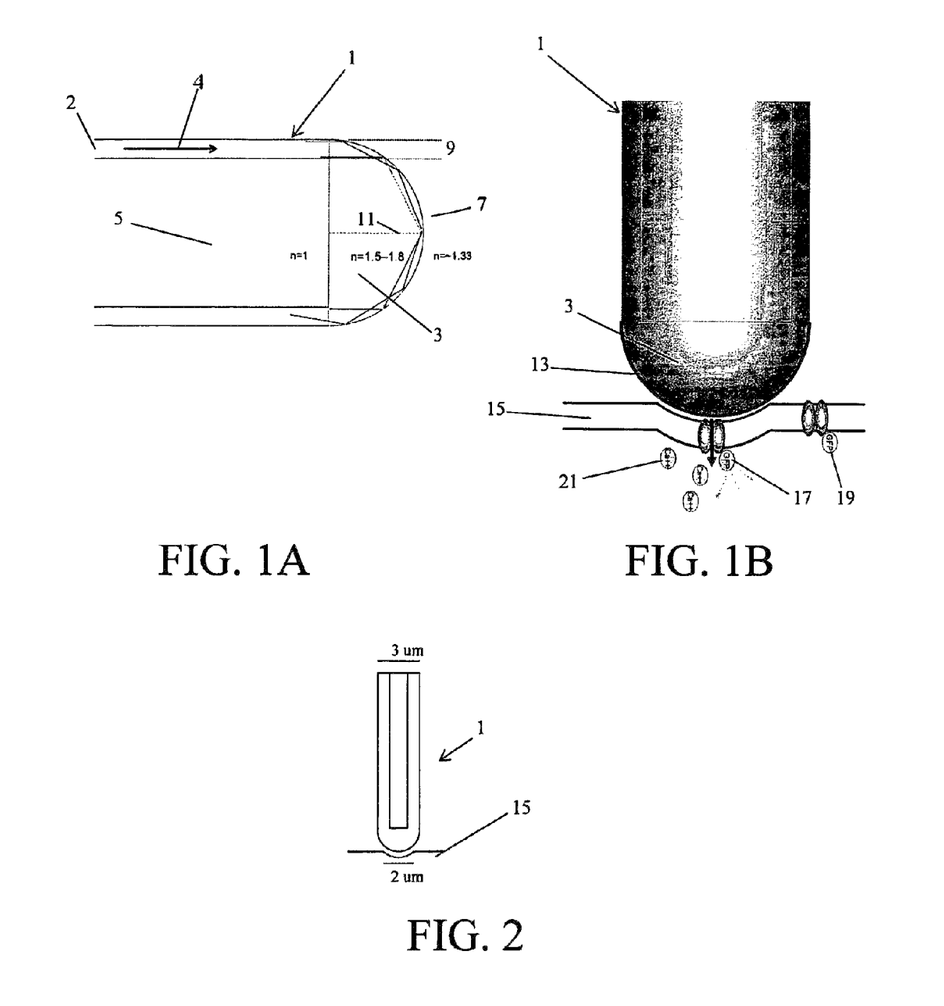
FIG. 1A is a schematic of the TIRF probe depicting the light path through the probe tip.
FIG. 1B is a drawing depicting the practical application of the TIRF probe.
FIG. 2 is a depiction of contact geometry for hemispherical lens with a cell membrane.

The optical probe of the present invention is designed to elicit total internal reflection fluorescence (TIRF) and generate an evanescent field on its internally reflecting tip. The evanescent field can then be used to excite fluorescent molecules in a highly controlled manner. By employing commercially available physiologically active dyes, point specific physiological measurements can be conducted. Additionally, this technique allows point specific imaging of fluorescent molecules without photobleaching other structures. Since the evanescent field is confined to a small patch of the cell surface and does not propagate, single molecule detection (e.g. GFP) correlated with specific coordinates and stimuli is possible (see FIG. 1). This technology is a highly accessible and inexpensive alternative to traditional electrophysiology techniques.

The novel optical probe of the present invention is capable of generating an evanescent field on the internally reflecting tip. In combination with commercially available physiologically active dyes, this probe can be used to interrogate cellular physiology. Additionally, the design can image individual fluorescent molecules due to the unique mode of fluorescent excitation. The probe allows ultra sensitive fluorescent imaging and cell physiology measurement and does not photobleach or excite undesired molecules. All emission can be attributed to the point of contact of the probe with a cell. The probe can be used as an optical alternative to an electrophysiology micropipette and is less complex and expensive as compared with electrophysiology.

The probe can be fabricated with a tip diameter of ~3 μm. Since only a portion of the hemispherical tip will be in direct contact with a cell, a 1-2 μm excitation patch is achieved (see FIG. 2). Additionally, an evanescent field can be reliably produced on the tip capable of exciting fluorescent molecules of interest.

An array of these probes can be arranged to conduct "Lab on a Chip" applications. A large number of assays can be conducted within a small footprint.

These and further and other objects and features of the invention are apparent in the disclosure, which includes the above and ongoing written specification, with the claims and the drawings.

DETAILED DESCRIPTION OF THE PREFERRED EMBODIMENTS

The present invention overcomes the limitations of traditional TIRF. An evanescent field can be generated on the tip of a specially designed glass or polymer probe. This probe technology will effectively allow researchers to conduct selective, point specific TIRF excitation and physiologic measurements. Since large areas of the sample are not illuminated and the energy does not propagate, the fluorescent molecules outside of the area of interest will not be exposed. Only excited molecules photobleach, thus the unbleached dye filling the rest of the cell will diffuse and displace the bleached dye; therefore, continuous and long term imaging can be conducted. This novel technology has the potential to excite and image single molecules, such as GFP linked G-proteins.

The present invention will mitigate much of the required expertise and expense of conducting traditional TIRF and electrophysiology. This is particularly true for nontraditional samples or experiments that will benefit from more basic physiologic measurement without being overwhelmed by the overhead of electrophysiology protocols. The technology will provide high quality physiologic data and will be accessible and relatively inexpensive for the consumer. This technology will not only benefit current research protocols, but will lead to unanticipated applications such as molecular sensors. The novelty of the approach also has the potential to be combined with traditional sharp and patch clamp electrophysiology protocols, which may reveal additional signaling information.

The technology can be used to conduct physiologic measurements and to conduct high resolution fluorescent imaging. The technology provides a solution that bridges two established markets—electrophysiology and physiologically active dyes. The present invention leverages the strengths of both these markets and making complex protocols more technically accessible and less expensive.

FIG. 1A is a schematic of the TIRF probe 1 depicting the light path from input end 2 through the probe tip 3, wherein the probe tip 3 is a closed. The differences in the refractive indices of the fluid within the probe 5, the probe 1, and the matter outside the probe 7 cause reflection of the light if the incident angle is greater than the critical angle. If the light meets the critical angle criteria, an evanescent field is generated on the tip. In this diagram, the interior of the probe has a refractive index of 1, as for air, the probe itself has an index of refraction of 1.4-1.8 (or greater), and the cell/tissue outside the probe has an index of refraction of ~1.33. The geometry of the hemispherical lens and the incoming light source 4 are important to ensure the critical angle is met. Computer models indicate that the radius 11 can be as small as 1.5 μm. The thickness of the probe body 9 can be up to about 12.3% of the radius 11 and still produce total internal reflection. These dimensions are dependent on the refractive indexes of the materials involved. For example, the potential radius may be larger or smaller.

FIG. 1B is a drawing depicting the practical application of the TIRF probe 1. An evanescent field 13 is generated on the tip of the probe 3, indicated by the blue surface. The tip of the probe 3 will contact a small section of the cell membrane 15 and excite molecules 17 in proximity. This is depicted by the emitting GFP molecule 17 at the probe tip 3 as compared with the non-emitting GFP molecule 19 that is not in direct contact. Additionally the tip 3 can be used to excite physiologically active dyes 21 (e.g. Ca++ sensitive dye) and elicit physiological data at the point of contact.

FIG. 2 is a diagram showing the probe 1 in contact with a cell membrane 15. The tip diameter of the probe is 3 µm and the width of the excitation patch is only 1-2 µm since only a portion of the hemispherical tip is in direct contact with the cell. An evanescent field is produced on the tip capable of exciting fluorescent molecules of interest.

Figure 7:
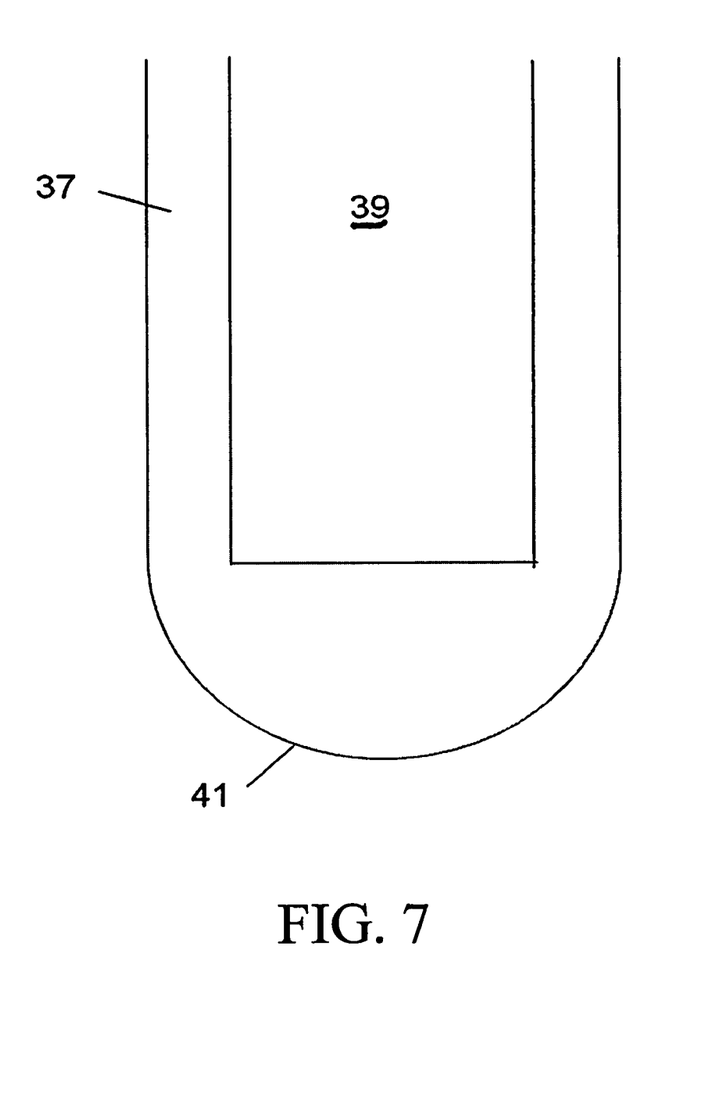
FIG. 7 is a diagram of a round probe surface probe configuration.
Figure 8:
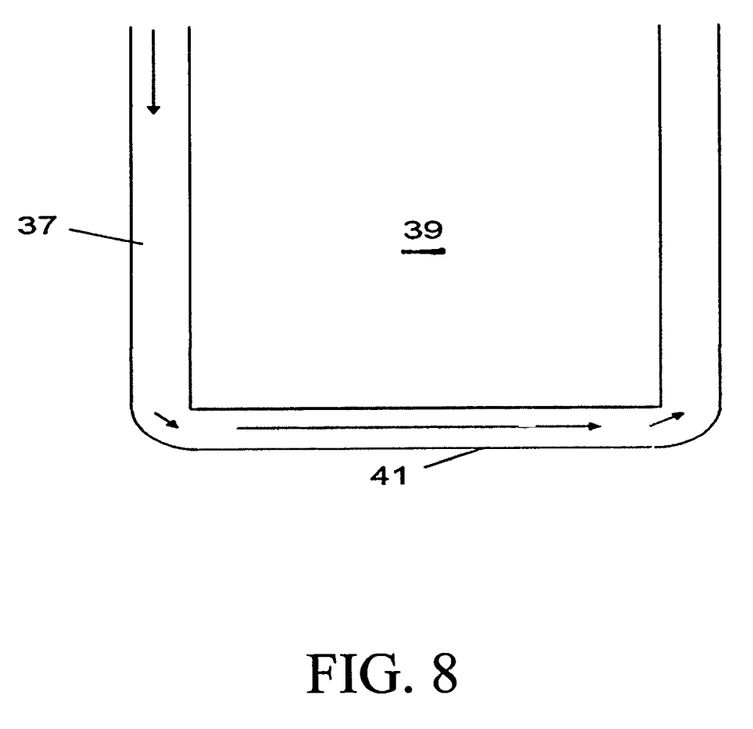
FIG. 8 is a diagram of a flat probe surface probe configuration.
Figure 9:
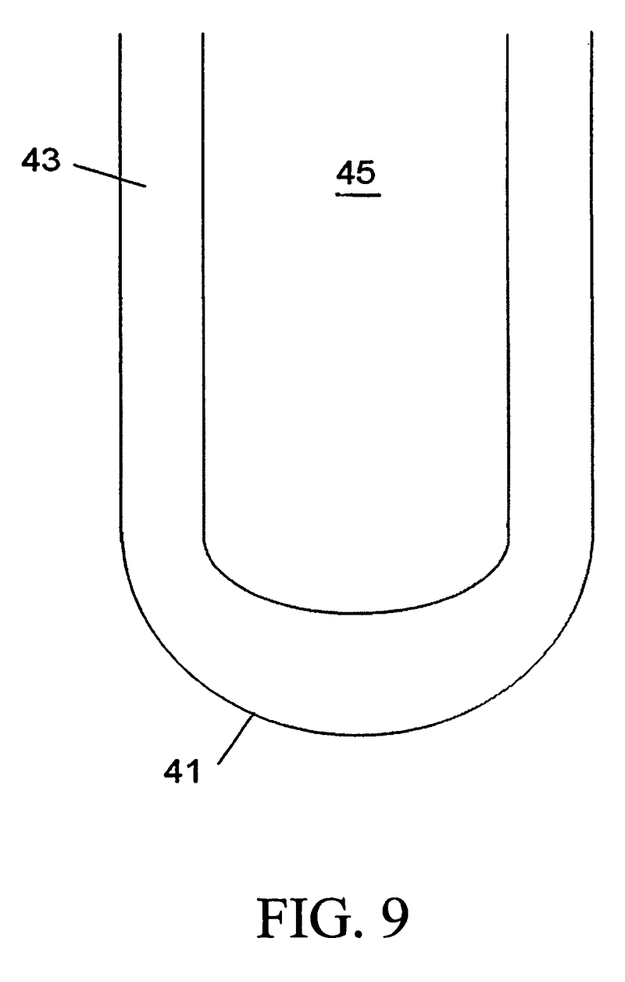
FIG. 9 is a diagram of a round probe surface optical fiber probe configuration or a polymer coated fiber.

FIGS. 7 to 9 are, without limitation, examples of other possible probe configurations. FIG. 7 illustrates a round probe surface probe configuration that is ideal for smaller samples or point specific interrogation. An optically transparent material 37 guides input light and has an nd greater than the interior 39 or exterior. Interior 39 may be air, gas, vacuum, or partially or completely filled with photon absorbing material and has a lower nd. Evanescent field generating surface 41 may be coated or uncoated.

FIG. 8 illustrates a flat probe surface probe configuration that is ideal for larger samples or cell trays. Again, an optically transparent material 37 guides input light and has an nd greater than the interior 39 or exterior. Interior 39 may be air, gas, vacuum, or partially or completely filled with photon absorbing material and has a lower nd. Evanescent field generating surface 41 may be coated or uncoated. FIG. 9 illustrates a round probe surface optical fiber probe configuration. This probe surface is fabricated from an optical fiber and is ideal for smaller samples or point specific interrogation. The tip is formed at the end of a cleaved fiber. Optical cladding 43 guides the input light and has a higher nd. The fiber core 45 has a lower nd. The evanescent field generating surface 41 may be coated or uncoated. This image could also represent an opaque fiber 45 coated with an optical polymer 43.

Light from sidewall 43 is trapped within the semi spherical end 41. Light in the interior 45 escaping blocking at proximal ends of probes 1 is trapped by CNTs which line the interiors.

Figure 10:
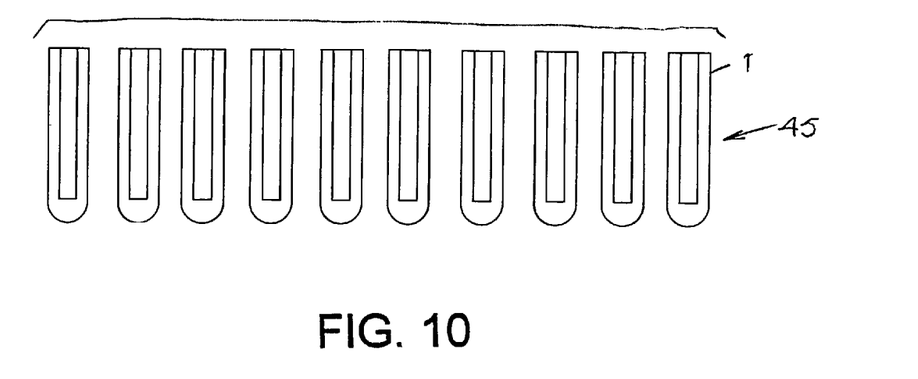
FIG. 10 schematically shows an array of probes.

FIG. 10 schematically shows an array 45 of probes 1. A number of probes are positioned in array 45 to test multiple samples of the same cell or tissue or multiple tissue or cells samples in a tray or other solution. This configuration would be ideal for molecular sensing such as DNA.

Computer Modeling

Figure 3A:
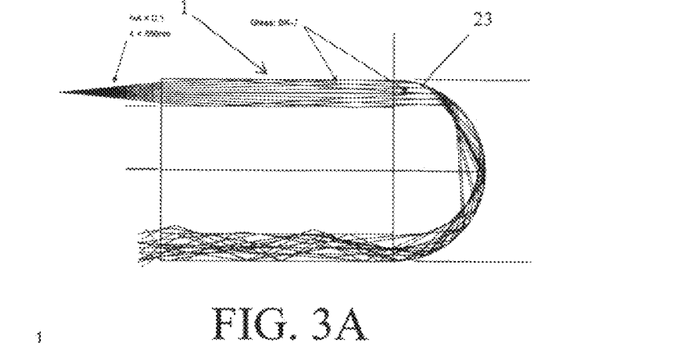
FIG. 3A is a 2D ray diagram showing the path of light rays within the probe.
Figure 3B:
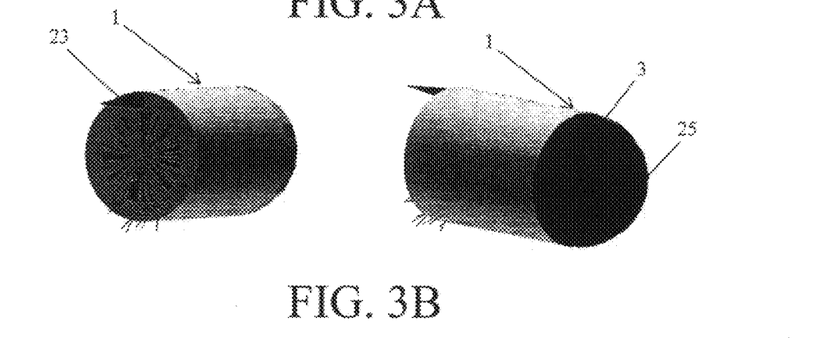
FIG. 3B is the 3D solid form model of the ray diagram.

Several design models were run to determine the theoretical limits of the TIRF probe. These models were used to find the proper combination of wavelengths, refractive indices, coupling mechanisms, etc. that result in total internal reflection on as small of a scale as possible. An example of the one of the models is shown in FIG. 3. It is well within optical principles to reduce the tip size to ~3 µm diameter and still achieve total internal reflection at a wavelength of 550 nm. The diameter may be reduced by modifying the refractive indexes involved.

FIG. 3 is an example computer model. The images are modeled using BK-7 glass (standard microscope glass), a wavelength of 550 nm, and assuming the refractive index of the fluid is 1.35 (the refractive index of standard mammalian cells). FIG. 3A is a 2D ray diagram showing the path of light rays 23 within the probe 1. Note that the rays 23 are internally reflected. FIG. 3B is the 3D solid form model of the previous ray diagram. Note the evanescent field 25 on the hemispherical tip 3 in the right panel—rays on the surface that do not propagate.

Prototype Probe Fabrication and Imaging Study

Prototype probes were fabricated using standard BK-7 glass. The probes were tested for evanescent field generation. The probe was coupled to a 488 nm laser via an air gap. Air gap coupling is a highly inefficient method; however, it was adequate to conduct the studies. The probe excitation field was imaged by submerging the tip into a dilute solution of QDots 605 (Invitrogen, Inc.). The solution approximated physiologic refractive indices. The probe tips were then imaged with brightfield microscopy, standard epifluorescence microscopy, and with a 488 nm laser coupled to the probe (see FIG. 4). Through this technique, the TIRF probe was demonstrated to be functional. FIG. 5 is an example of a probe that failed to generate an evanescent field; the laser energy propagated rather than internally reflecting.

Figure 4:
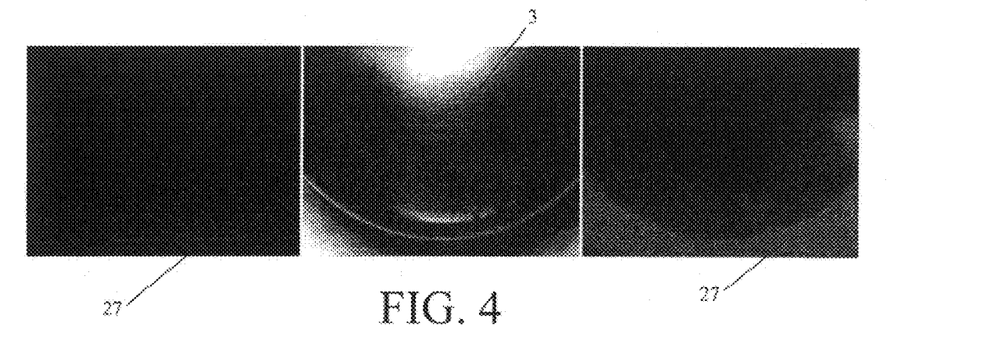
FIG. 4 is three images of the same probe tip profile and field using different imaging modes.
Figure 5:
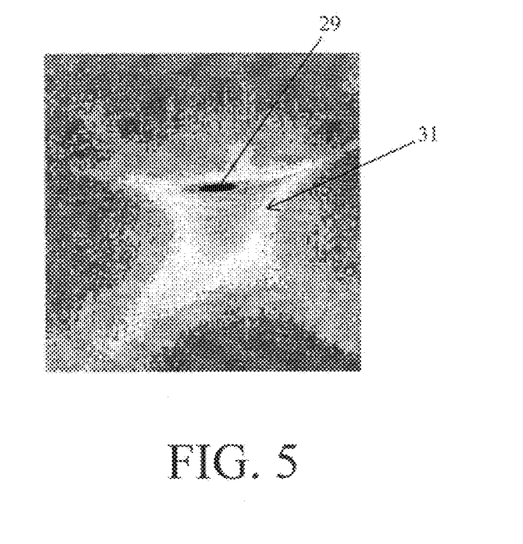
FIG. 5 is a spectrally enhanced image of a failed probe tip.

FIG. 4 shows three images of the same probe tip profile and field using different imaging modes. The images were taken using a 20× objective with a 1.6× multiplier. The tip was submerged in a solution of QDots 605. In FIG. 4A, the imaged quantum dots in this image were excited by the evanescent field via a 488 nm laser (blue). Emission filters were not placed in the image path. Only red quantum dot emission 27 is detected; the blue laser did not propagate. FIG. 4B shows a brightfield image of the probe tip 3. FIG. 4C is a traditional epifluorescence image of the same field. Note that the quantum dots are excited in widefield. The width of the image is about 50 µm.

FIG. 5 is a spectrally enhanced image of a probe tip similar to those shown in FIG. 4. The probe in this figure failed to generate an evanescent field. The laser energy propagated from the tip, as indicated by the evident rays 31 extending from the 'hot' spot 29 in the center of the image. This is an example of a failed probe.

Carbon Nanotube Catalytic Growth

To limit photon propagation inside the probe bore (see FIG. 1), a variety of materials may be used to act as photon traps. Carbon nanotubes (CNTs) have recently been shown to be the 'blackest' known material. CNTs can be fabricated and grown on surfaces such as the inside of the probe bore (see FIG. 6). Carbon nanotubes (CNTs) have been shown to be the most effective photon absorbing material ever described. CNT arrays can be 30× more photon absorbing than the black standard used by the National Institute of Standards and Technology. CNTs can be catalytically grown in the interior of the optical probe to act as a photon trap. This prevents stray photons from propagating from the tip of the probe. Alternative materials can be used in the bore of the probe to block or absorb stray photons. Stray photons may result in erroneous excitation and photobleaching. Using a specially designed deposition furnace, preferential radial CNT growth was successfully induced on the interior surface of a micropipette (see FIG. 6).

Figure 6:
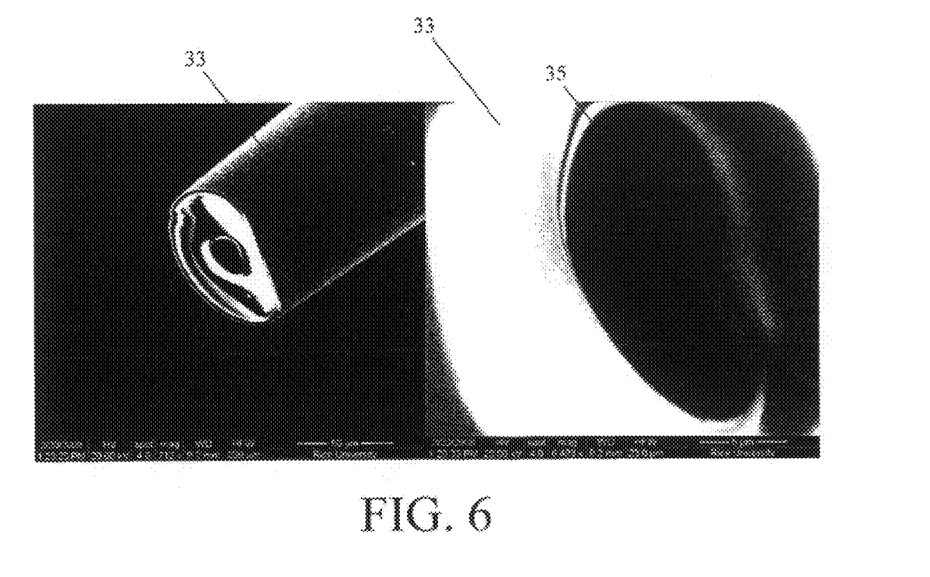
FIG. 6 is a SEM image of a cleaved micropipette tip with internal CNT growth.

FIG. 6 is a SEM image of a cleaved micropipette tip 33. The right panel is a 10× magnified view of the tip in the left panel. CNTs 35 were preferentially deposited on the interior surface of the micropipette.

Precise geometry is critical for total internal reflection generated evanescent fields. For reliably producing an evanescent field on a probe tip that approximates the size of a patchclamp micropipette (1-2 µm) the geometry becomes even more critical. Additionally, achieving highly confined excitation only at the tip of the probe requires the elimination of beam propagation or photon leakage. The probe tip is effectively a hemispherical lens. The curvature of the lens is highly uniform to achieve consistent total internal reflection.

Optic Fiber Coupling

Since the probe may be user positionable, the illumination may be fed to the probe via a fiber. In order to ensure reasonable efficiencies in the photo energy transfer from the fiber to the probe material, defects and refractive index differences are minimized. Several strategies can be employed to couple the light source to probe. Strategies might include without limitation

- direct arc coupling
- focusing or collinating the light into the glass walls of the probe
- a basic air gap
- applying a collecting lens or forming the input end of probe into a collecting lens
- using optical matching gels or adhesives Since many of the dyes and fluorescent molecules (e.g. GFP) excite in the ultraviolet and lower half of the visual spectrum, the probe design may preferably be optimized for this range (350 nm-500 nm). The wavelength, in part, will determine optimal fiber and fiber cladding options. Coupling the 488 nm laser through an air gap is relatively crude but effective. Efficiency can be improved by orders of magnitude and repeatability can be ensured by refining this system. The laser input end of the probe may be pulled into a fiber that can be directly coupled with the laser fiber guide. Alternatively, fiber collimating lens and/or a variety of refractive index matching compounds (optical gels and oils) can be employed. An axiconic lens could also be included to produce a hollow cylinder of laser light matching the diameter of probe input end. An axiconic lens is a conical lens that converts a beam of light into a virtual tube of light.

Probe Material Selection

Standard borosilicate glass (nd ~1.5) may be used; however, there are a wide variety of materials that have more desirable qualities. With a higher refractive index probe material (e.g. nd 1.8), the probe tips can be made smaller because it more effectively internally reflects light within smaller curvatures. The availability of the materials, costs, and whether it is prefabricated as capillary tubing are all considerations in deciding what material to use.

Practical Excitation Testing

A microscopic imaging technique has been established to examine whether an evanescent field is generated on the probe tip (see FIG. 4). A dilute solution of quantum dots (e.g. QDot 605 from Invitrogen, Inc.) are prepared with physiologic solution (DMEM with 10% bovine serum). This solution was selected to most closely approximate the refractive index of practical applications. The exact quantum dot dilution is adjusted to the relative energy transfer efficiencies achieved. The test probe is affixed to a microscope slide, parallel to the slide surface and perpendicular to the microscope observation path. A testing rig is constructed to ensure proper orientation. An aliquot of the quantum dot solution is applied at the tip of the affixed probe. The tip of the probe is completely covered by the solution. In this configuration, the laser energy will then excite quantum dots, which can be imaged microscopically.

If the probe fails to produce an evanescent field, rays of excitation propagate from the probe tip; however, if an evanescent field is produced, excitation is limited to the surface of the probe curvature and does not propagate. The excitation distance is measured by imaging the resulting emission. Since the evanescent field (~100 nm) is considerably smaller than the wavelength of the fluorescent emission (605 nm), only the emission can be measured. The resultant fluorescent emission from an evanescent field behaves as a point source of light and therefore is no more one wavelength from the surface of the probe. For example, if the emission field extends 2 microns from the tip, this would indicate photon leakage or propagation.

ADDITIONAL ADVANTAGES

Selective excitation of small, confined regions is required in order to conduct physiologic measurements. Additionally, the detection of individual fluorescent molecules requires highly controlled excitation to prevent erroneous excitation or unintentional photobleaching. The selective and specific TIRF excitation of small portions of the membrane improves the possibility of detecting extremely low signal strength since many of the signal limiting factors can be eliminated. There are no excitation or emission filters required since the excitation energy does not propagate and only the resulting emission light will be available to the objective lens.

Additionally and unlike classic TIRF imaging, using an array based imaging device (e.g. such as a CCD digital camera) is not necessary while using the technology. A phototube multiplier can be used to greatly increase the realized sensitivity; therefore any detected photons can be attributed to the probe coordinates. This is similar to the way confocal based microscopy increases sensitivity by scanning and reconstructing the image pixel by pixel. As an example, if a single molecule of GFP is excited by the TIRF probe, all resulting photons can be attributed to the specific coordinates and time. This same concept can be applied to the variety of molecular probes and dyes.

High Resolution Scan Imaging

The present invention may be used as a scanning probe. By scanning the probe tip over sections of the membrane, an image can be reconstructed pixel by pixel. This technique can result in a high resolution fluorescent image that exceed the diffraction limit resolution of traditional optical microscopes. This scanning method is similar to near-field scanning microscopy. Since the image is reconstructed pixel by pixel, resolution is defined by the area of excitation rather than diffraction limitations. As the leading edge of the scanning probe excites a new molecule, the molecule is attributed to the x/y coordinates of the probe. Ideally the molecule will be bleached and newly encountered molecules will provide the coordinate specific data. Since an evanescent field is approximately 100 nm, the resolution of the system can approach this value.

Sensitivity and Signal to Noise

Since the probe selectively and specifically excites small sections (1-2 µm) of cellular membrane and structures, it is able to image surface structures with better signal to noise ratio than standard wide-field fluorescence excitation. The sensitivity of the system is also significantly better.

Physiologic Measurements

The present invention provides a practical technique to interrogate cell physiology. By combining this probe with commercially available physiologic dyes, precise physiologic measurements (e.g. calcium or sodium conductance) can be conducted that previously required complex electrophysiology equipment. Moreover, these measurements can be attained without damaging the imaged cell. The present invention will allow users to conduct similar measurement to electrophysiological techniques without the technical complexity and expense of electrophysiological system.

Point specific optical physiological measurements can effectively be conducted using the TIRF probe. The measurements are sufficiently comparable to standard electrophysiology to be useful in a wide variety of applications. Additionally, the technique is not as technically demanding as electrophysiology techniques and therefore is more accessible to a wider range of researchers. Using the TIRF probe allows far more localized physiological measurements using fluorescent dyes as compared with the traditional wide-field imaging protocols. The probe will not damage or alter the imaged cells.

The present invention is a novel approach for interrogating cellular physiology and signaling using a unique form of total internal reflection fluorescence (TIRF) excitation. This TIRF-based technique can be used to conduct non-invasive cellular physiology measurements. Wide varieties of physiologic dyes have recently been developed and improved (e.g. calcium, sodium, and voltage sensitive dyes). The TIRF probe of the present invention can be used to conduct point specific measurements much like an electrophysiology electrode. Since the evanescent field is confined to a small patch of the cell surface and does not propagate, single molecule detection (e.g. GFP) correlated with specific coordinates and stimuli is possible.

Array Configurations and Molecular Sensing

The invention may be used individually or in an array configuration to detect molecules of interest. An example of this technique might involve functionalizing the individual probes by various DNA molecules to conduct rapid DNA sequencing. Another example of molecular sensing might involve placing a probe or array of probes in a static of flowing solution. The probes may be functionalized to be sensitive to various target molecules.

While the invention has been described with reference to specific embodiments, modifications and variations of the invention may be constructed without departing from the scope of the invention, which is defined in the following claims.

I claim:

1. Evanescent cell probes comprising:
micropipette probes having walls with input ends and closed tips,
the closed tips having internal closed opposite end light reflector surfaces,
light sources coupled to the walls at the open ends for conducting photons through the walls to the tips for total internal reflection of the photons by the reflector surfaces at the closed tips,
micro evanescent fields created at the closed tips for exciting fluorescent molecules at the closed tips,
further comprising photon absorbing material disposed in internal spaces of the micropipette probes.

2. The evanescent cell probes of claim 1, wherein the photon absorbing material such as is carbon nanotubes in the internal spaces of the micropipette probes.

3. The evanescent probes of claim 1, wherein the micropipette probes are mounted in an array of micropipette probes for creating an array of evanescent fields at the closed tips of the micropipette probes.

4. The evanescent probes of claim 1, wherein the closed ends are hemispherical tips having diameters of about 3 µm or less or larger.

5. The evanescent probes of claim 4, wherein the cell contact areas are about 1-2 µm or less.

6. The evanescent probes of claim 1, wherein the evanescent fields have cell penetrations of about 100 nm or less.

7. A method of studying cell physiology comprising:
providing at least one cell,
applying physiologic fluorescent dye to the cell,
providing a micropipette probe having a wall, a light input end and an opposite closed tip with total internal light reflection,
providing an illumination at the input end,
conducting the illumination output through the wall of the micropipette probe to the closed tip,
totally internally reflecting the illumination at the closed tip,
producing an evanescent field at the closed tip of the micropipette probe,
exciting fluorescence of a dyed part of the cell with the evanescent field at the tip of the micropipette probe, and
sensing the fluorescence at the tip of the micropipette,
further comprising photon absorbing material in internal spaces of the micropipette probe.

8. The method of claim 7, wherein the cell is a live cell, membrane or tissue.

9. A method of studying cell physiology comprising:
providing at least one cell,
applying physiologic fluorescent dye to the cell,
providing a micropipette probe having a wall, a light input end and an opposite closed tip with total internal light reflection,
providing an illumination at the input end,
conducting the illumination output through the wall of the micropipette probe to the closed tip,
totally internally reflecting the illumination at the closed tip,
producing an evanescent field at the closed tip of the micropipette probe,
exciting fluorescence of a dyed part of the cell with the evanescent field at the tip of the micropipette probe, and
sensing the fluorescence at the tip of the micropipette,
further comprising:
providing plural micropipette probes having closed tips with total internal light reflection,
assembling the plural micropipette probes in an array,
providing illumination of single or multiple wavelengths to input ends of the micropipette probes,
totally internally reflecting the illuminating in the closed tips of the micropipette probes,
producing separate evanescent fields at the closed tips of the micropipette probes, and separately exciting of molecules with the separate evanescent fields at the tips of the micropipette probes, and
sensing emissions at the tips of the micropipette probes.

10. The method of claim 9, wherein the micropipette probes have hemispherical tips and further comprising touching cell membranes with parts of the tips.

11. The method of claim 9, wherein the hemispherical tips have diameters of about 3 µm or less, and wherein the touching comprises touching areas of about 1.2 µm diameters.

12. The method of claim 11 further comprising producing the evanescent fields up to about 100 nm from tips and exciting fluorescence in touched areas at a penetration depth of about 100 nm from the tips.

13. The method of claim 9, wherein the cell is a live cell, membrane or tissue.

14. The method of claim 9, wherein the sample is a fluid or gas.

15. The method of claim 9, further comprising providing photon absorbing material in internal spaces of the micropipette probes.

16. The method of claim 15, wherein the providing photon absorbing material in internal spaces of the micropipette probes further comprises providing carbon nanotubes in the internal spaces of the micropipette probes.

17. The method of claim 9, wherein the tips are generally flat.

18. The evanescent cell probes of claim 1, where the tips are generally flat.

* * * * *